(12) United States Patent
Barnell et al.

(10) Patent No.: US 10,117,720 B2
(45) Date of Patent: Nov. 6, 2018

(54) DEVICE RETENTION MECHANISM AND METHOD

(71) Applicant: Medtronic Vascular, Inc., Santa Rosa, CA (US)

(72) Inventors: Jeffrey Barnell, Santa Rosa, CA (US); Courtney Spens, Santa Rosa, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 0 days.

(21) Appl. No.: 15/332,968

(22) Filed: Oct. 24, 2016

(65) Prior Publication Data

US 2018/0008799 A1 Jan. 11, 2018

Related U.S. Application Data

(60) Provisional application No. 62/359,049, filed on Jul. 6, 2016.

(51) Int. Cl.
*A61B 50/36* (2016.01)
*A61B 50/33* (2016.01)
(Continued)

(52) U.S. Cl.
CPC ........ *A61B 50/36* (2016.02); *A61B 17/00234* (2013.01); *A61B 50/33* (2016.02);
(Continued)

(58) Field of Classification Search
CPC ........ B65D 25/101; B65D 25/10; B65D 1/34; B65D 43/0202; F04B 43/08;
(Continued)

(56) References Cited

U.S. PATENT DOCUMENTS 4,678,462 A * 7/1987 Vaillancourt ......... A61M 25/02
 128/877
5,742,487 A * 4/1998 Kobayashi ............... B25J 15/04
 206/560
(Continued)

FOREIGN PATENT DOCUMENTS

CA 907570 8/1972
EP 2106821 A1 10/2009
(Continued)

OTHER PUBLICATIONS

U.S. Appl. No. 62/359,049, of Jeffrey Barnell, titled "Hybrid Sealed Tray For Long Catheter Delivery Systems", filed Jul. 6, 2016.
(Continued)

*Primary Examiner* — Rafael Ortiz

(57) ABSTRACT

A device retention assembly includes a delivery system and a device retention mechanism retaining the delivery system. The device retention mechanism includes a tray, a base coupled to the tray, and retaining flanges pivotally coupled to the base. The delivery system is enclosed within an opening defined by the base and retaining flanges. A key locks the device retention mechanism in the closed position retaining the delivery system. The key must be removed to unlock the device retention mechanism to release the delivery system.

7 Claims, 17 Drawing Sheets

(51) Int. Cl.
| | |
|---|---|
| *A61B 17/00* | (2006.01) |
| *A61F 2/95* | (2013.01) |
| *B65B 7/02* | (2006.01) |
| *B65D 1/34* | (2006.01) |
| *A61F 2/00* | (2006.01) |
| *A61M 25/00* | (2006.01) |
| *B65D 25/10* | (2006.01) |
| *B65D 43/02* | (2006.01) |
| *A61B 50/30* | (2016.01) |
| *A61L 2/20* | (2006.01) |

(52) U.S. Cl.
CPC .............. *A61F 2/0095* (2013.01); *A61F 2/95* (2013.01); *A61M 25/002* (2013.01); *B65B 7/02* (2013.01); *B65D 1/34* (2013.01); *B65D 25/10* (2013.01); *B65D 43/0202* (2013.01); *H05K 999/99* (2013.01); *A61B 2017/00362* (2013.01); *A61B 2050/314* (2016.02); *A61L 2/206* (2013.01)

(58) Field of Classification Search
CPC .... A61M 25/002; A61F 2/0095; A61B 50/36; A61B 50/33; A61B 17/00234; B65B 7/02
USPC ....... 206/363, 364, 565, 560, 477, 559, 571, 206/562; 248/592, 593, 595; 604/174, 604/175, 178; 220/737, 743, 23.89, 23.87
See application file for complete search history.

(56) References Cited

U.S. PATENT DOCUMENTS

| | | | | |
|---|---|---|---|---|
| 6,428,515 | B1* | 8/2002 | Bierman | ............... A61M 25/02 128/DIG. 26 |
| 7,160,270 | B2* | 1/2007 | West | .................. A61B 1/00154 128/DIG. 26 |
| 2005/0038453 | A1 | 2/2005 | Raulerson | |
| 2009/0306603 | A1 | 12/2009 | Bierman et al. | |
| 2012/0305441 | A1 | 12/2012 | Murray et al. | |
| 2015/0068939 | A1 | 3/2015 | Seitz, III | |

FOREIGN PATENT DOCUMENTS

| | | |
|---|---|---|
| EP | 2468346 A1 | 6/2012 |
| EP | 2609955 A1 | 7/2013 |
| EP | 2609956 A1 | 7/2013 |
| JP | 2011139882 A | 7/2011 |
| WO | 2002/47602 A2 | 6/2002 |
| WO | WO0247602 A2 | 6/2002 |
| WO | 2005/092419 A1 | 10/2005 |
| WO | WO2005092419 A1 | 10/2005 |
| WO | 2012/079590 A1 | 6/2012 |
| WO | 2015/047455 A2 | 4/2015 |
| WO | 2015/089189 A2 | 6/2015 |
| WO | 2015/089197 A2 | 6/2015 |

OTHER PUBLICATIONS

U.S. Appl. No. 15/277,509, of Jeffrey Barnell, titled "Hybrid Sealed Tray For Long Catheter Delivery Systems", filed Sep. 27, 2016.
U.S. Appl. No. 15/277,537, of Jeffrey Barnell, titled "Biomatter Capture Mechanism And Method", filed Sep. 27, 2016.
U.S. Appl. No. 15/333,287, of John Gallagher, titled "Hinged Long Sealed Tray and Method", filed Oct. 25, 2016.
U.S. Appl. No. 15/333,317, of John Gallagher et al., titled "Slip Card For Long Sealed Trays And Method", filed Oct. 25, 2016.
PCT/US2017/040587, The International Search Report and the Written Opinion of the International Searching Authority, dated Sep. 29, 2017, 13 pages.
PCT/US2017/040590, The International Search Report and the Written Opinion of the International Searching Authority, dated Sep. 29, 2017, 15 pages.
PCT International Search Report corresponding to International Application No. PCT/US2017/040587; dated Sep. 29, 2017, 13 pages.
PCT International Search Report corresponding to International Application No. PCT/US2017/040589, dated Sep. 27, 2017, 6 pages.

* cited by examiner

DEVICE RETENTION MECHANISM AND METHOD

RELATED APPLICATIONS

This application claims the benefit of U.S. Provisional Application No. 62/359,049 filed on Jul. 6, 2016, entitled "HYBRID SEALED TRAY FOR LONG CATHETER DELIVERY SYSTEMS" of Jeffery Barnell, which is incorporated herein by reference in its entirety.

BACKGROUND

Field

The present application relates to packaging for an intra-vascular device and method. More particularly, the present application relates to packaging for a device for treatment of intra-vascular diseases and related methods.

Description of the Related Art

A delivery system is contained within a container using a variable interference fit, which uses friction between the delivery system and a corresponding opening in the container. However, tolerance in the formation of the opening and in the delivery system leads to inconsistency in the variable interference fit. If the variable interference fit is too loose, the delivery system may become dislodged from the container and damaged, e.g., during transportation. Conversely, if the variable interference fit is too tight, excess force to remove the delivery system from the opening may be required, again possibly damaging the delivery system and at least presenting an inconvenience during removal of the delivery system.

SUMMARY

A device retention assembly includes a delivery system and a device retention mechanism retaining the delivery system. The device retention mechanism includes a tray, a base coupled to the tray, and retaining flanges pivotally coupled to the base. The delivery system is enclosed within an opening defined by the base and retaining flanges. A key locks the device retention mechanism in the closed position retaining the delivery system. The key must be removed to unlock the device retention mechanism to release the delivery system.

The device retention mechanism eliminates accidental dislodgement and damage of the delivery system, e.g., during transportation, as removal of a mechanical key (e.g., a device removal assist card) is required. Further, the device retention mechanism has less potential for damaging the delivery system during removal as compared to a variable interference fit, which sometimes requires excess force to remove.

These and other features in accordance with various embodiments will be more readily apparent from the detailed description set forth below taken in conjunction with the accompanying drawings.

BRIEF DESCRIPTION OF DRAWINGS

Common reference numerals are used throughout the drawings and detailed description to indicate like elements.

DETAILED DESCRIPTION

Figure 1:
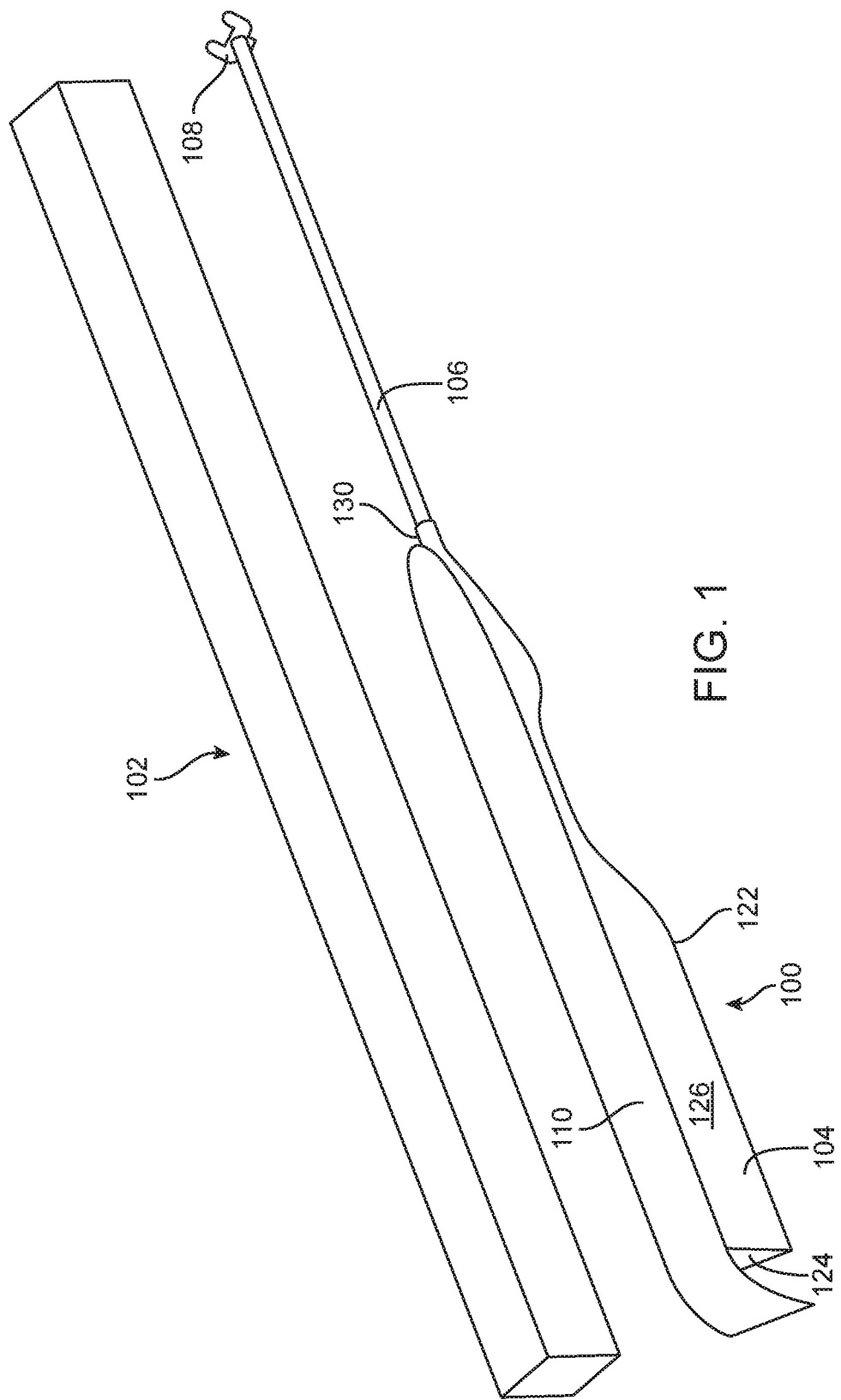
FIG. 1 is a perspective view of a catheter delivery system package and a shelf carton in accordance with one embodiment.
Figure 2:
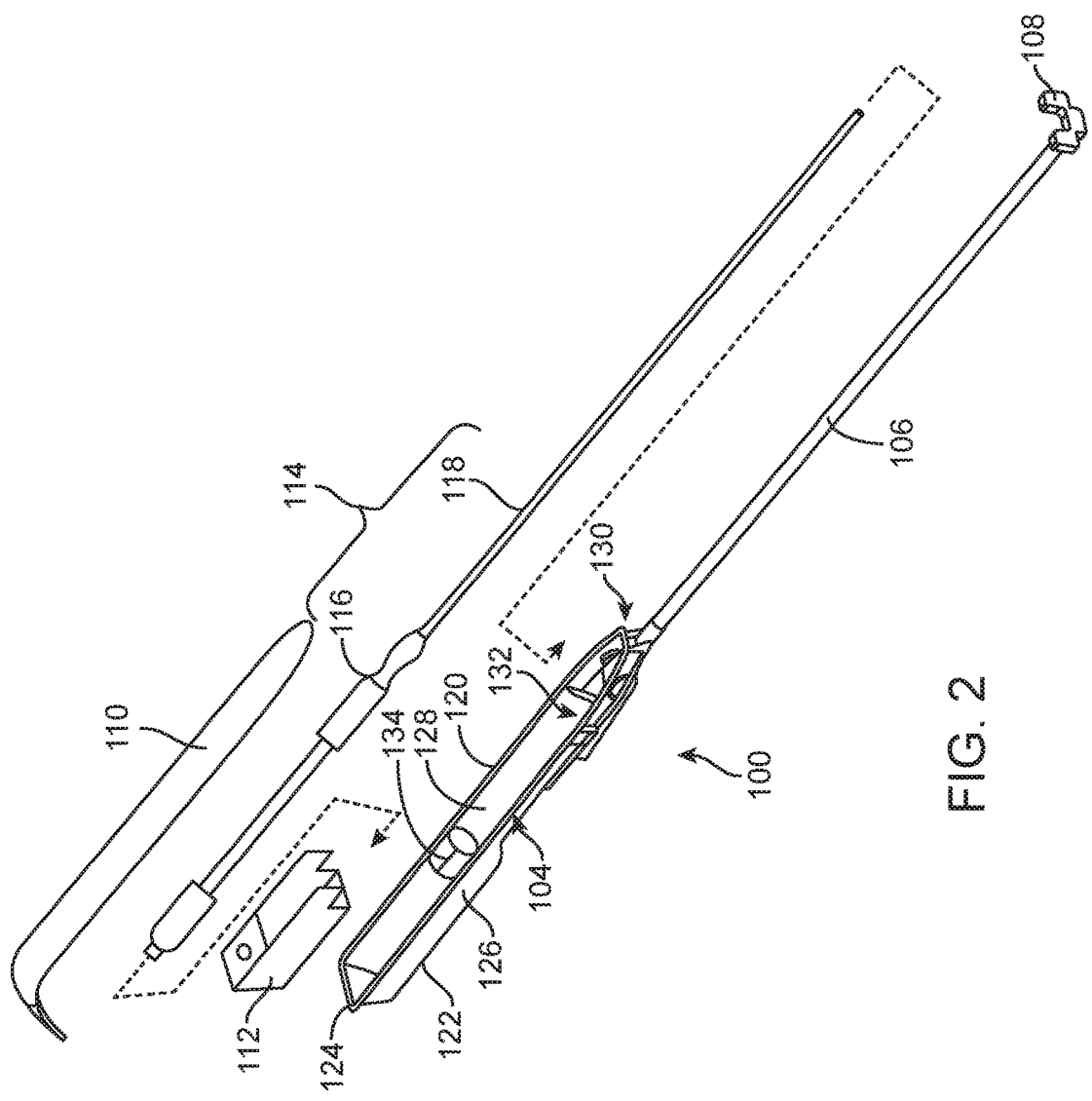
FIG. 2 is an exploded perspective view of the catheter delivery system package of FIG. 1 in accordance with one embodiment.

FIG. 1 is a perspective view of a catheter delivery system package 100 and a shelf carton 102, sometimes called a box, in accordance with one embodiment. FIG. 2 is an exploded perspective view of catheter delivery system package 100 of FIG. 1 in accordance with one embodiment.

Referring to FIGS. 1-2 together, catheter delivery system package 100 is transported or otherwise contained inside of shelf carton 102. Catheter delivery system package 100 includes a tray 104, an extension tube 106, an end cap 108, a lid 110, and a device removal assist card 112. Catheter delivery system package 100 is a sterile container package for a delivery system 114. Delivery system 114 include a handle 116 and a protruding portion 118 protruding from handle 116. Examples of delivery system 114 includes the Valiant™ Aortic Stent Graft System although other delivery systems are used in other embodiments.

In one embodiment, delivery system 114, e.g., a medical device, includes one or more stents, grafts, stent-grafts, or other endoluminal devices for delivery and implantation within a patient. Protruding portion 118, e.g., a delivery system catheter, is cylindrical in accordance with one embodiment and is configured to be inserted into a patient. Protruding portion 118 is not limited to a cylindrical member and can take various shapes and have various features in accordance with other embodiments.

Tray 104, sometimes called a common injection-molded body, is a hybrid sealed tray in one embodiment. Tray 104 includes an integral lid sealing flange 120 for sealing with lid 110. Tray 104 contains handle 116 of delivery system 114 therein. In various embodiments, tray 104 is formed using injection molding, blow molding, or thermoformed. Examples of suitable trays are set forth in Barnell, U.S. patent application Ser. No. 15/277,509, filed Sep. 27, 2016 and Barnell, U.S. patent application Ser. No. 15/277,537, filed Sep. 27, 2016, which are both herein incorporated by reference in their entirety.

Tray 104 includes a bottom surface 122, a proximal end 124, sides 126, 128, and a distal end 130. Extension tube 106 is coupled to distal end 130 of tray 104. Sides 126, 128 and ends 124, 130 extend upward and away from bottom surface 122 to lid sealing flange 120. Sides 126, 128 extend opposite one another and between proximal end 124 and distal end 130. Similarly, proximal end 124 and distal end 130 extend opposite one another and between sides 126, 128.

As used herein, the distal end of delivery system 114 is identified as the end that is farthest from the operator (handle 116) while the proximal end of delivery system 114 is the end nearest the operator (handle 116). Similarly, the distal end of catheter delivery system package 100 is identified to the end that is farthest from tray 104 (handle 116) while the proximal end of catheter delivery system package 100 is the end nearest tray 104 (handle 116).

End cap 108 hermetically seals the distal end of extension tube 106. Extension tube 106 in combination with tray 104 define a delivery system cavity 132 into which delivery system 114 is placed and sealed in a sterile condition. Generally, delivery system cavity 132 is a sterile sealed cavity defined by tray 104, extension tube 106, end cap 108 and lid 110.

More particularly, protruding portion 118 is slid into extension tube 106 though tray 104. Protruding portion 118 is slid into extension tube 106 until handle 116 is located within tray 104. Tray 104 includes a device retention mechanism 134 for retaining handle 116 as discussed further below. In one embodiment, device removal assist card 112, sometimes called a slip card, is a key for device retention mechanism 134 and is inserting into tray 104 with or before handle 116. Generally, delivery system 114 is placed within delivery system cavity 132.

After delivery system 114 is placed in tray 104 and extension tube 106, the sterile barrier is created with the additional of lid 110, e.g., a sealed Tyvek or other film lid.

Although a particular tray 104 is illustrated in FIGS. 1-2, in accordance with other embodiments, tray 104 can take a wide variety of shapes and sizes, e.g., can be an open tray, depending upon the particular application. For example, an open tray including handle 116 are contained in a sterile condition within a sterile barrier pouch. The entire assembly including the open tray, extension tube 106, end cap 108, and delivery system 114 are contained within a sterile barrier pouch.

In the following description, tray 104, extension tube 106, end cap 108, and delivery system 116 of catheter delivery system package 100 of FIGS. 1-2 are discussed. However, in light of this disclosure, those of skill in the art will understand that the following description is equally applicable to any one of a number of structures, e.g., an open tray, having device retention mechanism 134 for retaining delivery system 114.

Figure 3:
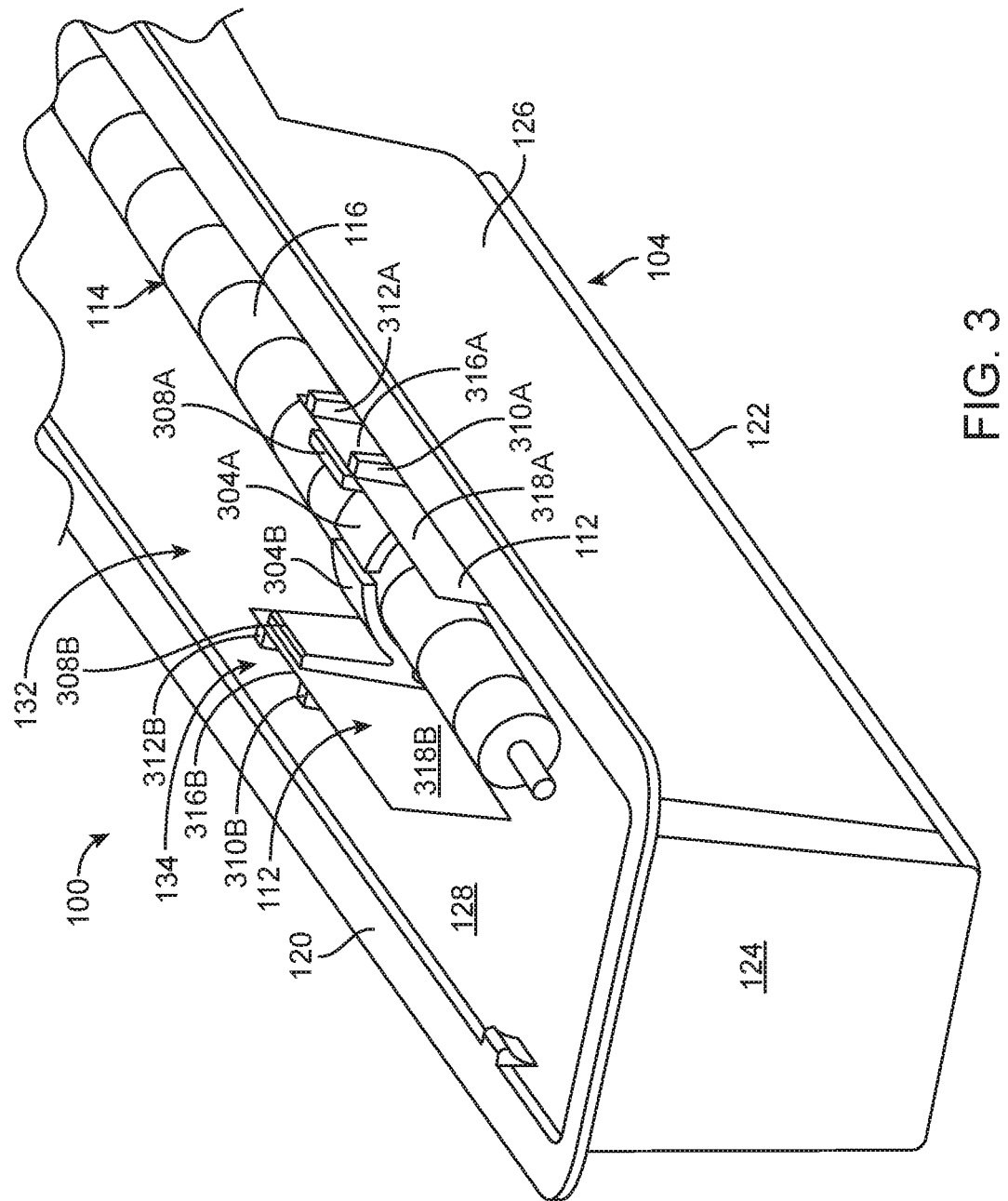
FIG. 3 is a perspective view of a device retention mechanism retaining a handle of a delivery system within a tray of the catheter delivery system package of FIGS. 1 and 2 in accordance with one embodiment.
Figure 4:
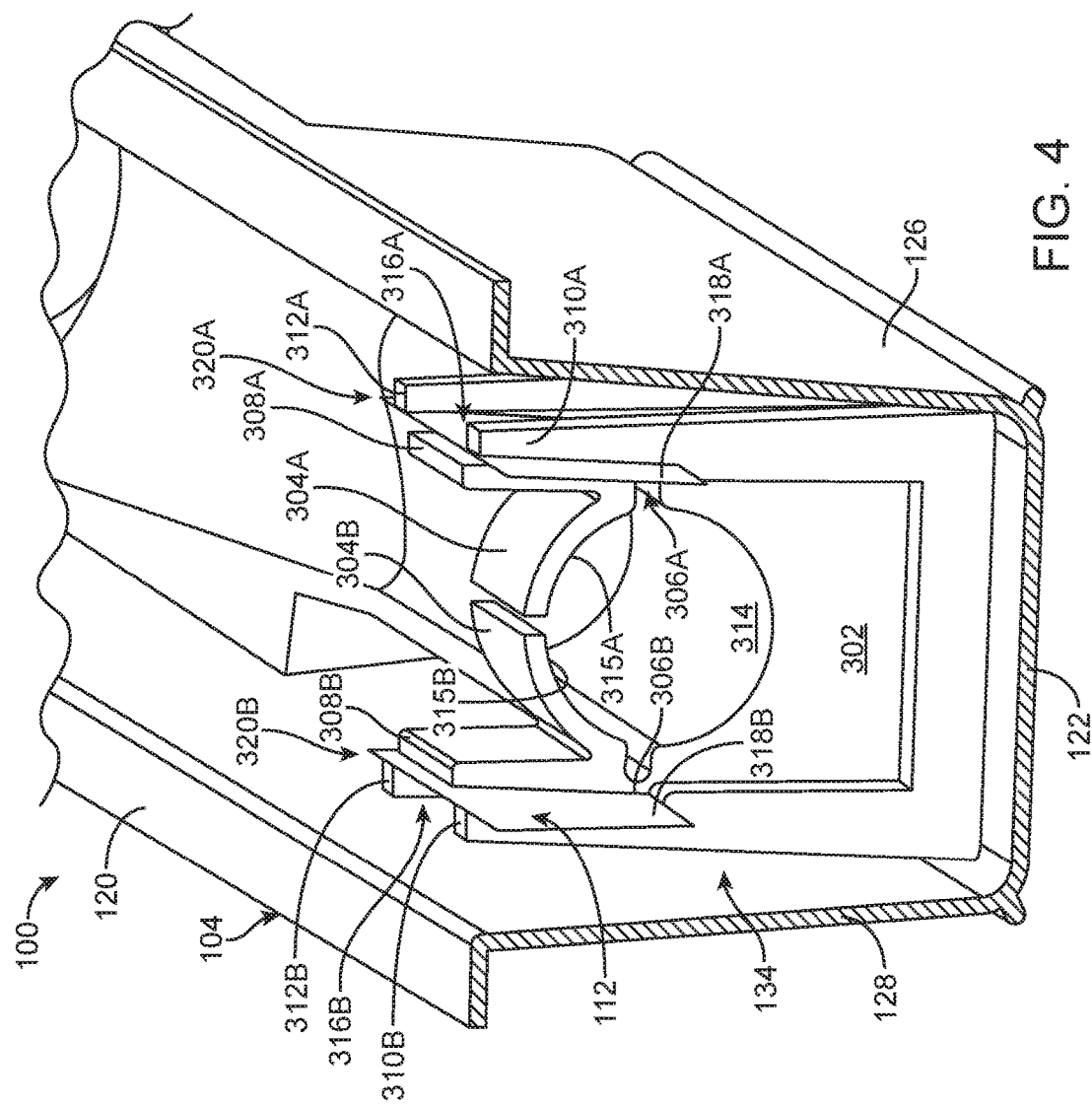
FIG. 4 is a perspective cross-sectional view of the device retention mechanism of FIG. 3 in accordance with one embodiment.

FIG. 3 is a perspective view of device retention mechanism 134 retaining handle 116 of delivery system 114 within tray 104 of catheter delivery system package 100 of FIGS. 1 and 2 in accordance with one embodiment. FIG. 4 is a perspective cross-sectional view of device retention mechanism 134 of FIG. 3 in accordance with one embodiment. In FIGS. 3-4, device removal assist card 112 is cutoff to allow visualization of device retention mechanism 134. Further, in FIG. 4, handle 116 has been removed to allow visualization of device retention mechanism 134.

Device retention mechanism 134 includes a fixed base 302, retaining flanges 304A, 304B, pivots 306A, 306B, locking plates 308A, 308B, proximal locking plate retaining posts 310A, 310B, and distal locking plate retaining posts 312A, 312B. Generally, retaining flange 304B, pivot 306B, locking plate 308B, proximal locking plate retaining post 310B, and distal locking plate retaining post 312B are mirror images of retaining flange 304A, pivot 306A, locking plate 308A, proximal locking plate retaining post 310A, and distal locking plate retaining post 312A, respectively. However, in another embodiment, device retention mechanism 134 is not symmetrical, e.g., has only one long arm.

Fixed base 302 is fixed in position, e.g., is part of tray 104 or secured to tray 104. Fixed base 302 is shaped to receive the device being retained. More particularly, fixed base 302 includes a semi cylindrical device retaining surface 314, i.e., having the shape of half of a cylinder divided lengthwise, complimentary to the shape of handle 116. Device retaining surface 314 can take various shapes complimentary to the shape of handle 116, e.g., can be tapered, have protrusions, indentations, or other features depending on the particular shape of handle 116 in various embodiments.

Retaining flanges 304A, 304B, sometimes called gates, are pivotally coupled to fixed base 302 by pivots 306A, 306B, e.g., thin molded strips, pins, or hinges, respectively. Retaining flanges 304A, 304B pivot around pivots 306A, 306B to move retaining flanges 304A, 304B from the closed position around handle 116 to an open position for removal of handle 116 as discussed further below. In the closed position, retaining flanges 304A, 304B abut one another.

Retaining flanges 304A, 304B are shaped to retain the device being retained. More particularly, retaining flanges 304A, 304B include quarter cylindrical device retaining surfaces 315A, 315B, respectively, having the shape of quarter of a cylinder divided lengthwise, complimentary to the shape of handle 116. Device retaining surfaces 315A, 315B can take various shapes complimentary to the shape of handle 116, e.g., can be tapered, have protrusions, indentations, or other features depending on the particular shape of handle 116 in various embodiments. In one embodiment, device retaining surfaces 314, 315A, 315B collectively define a cylindrical surface and a cylindrical opening therein.

Locking plates 308A, 308B are integral parts of retaining flanges 304A, 304B, respectively, in accordance with this embodiment. Locking plates 308A, 306B are parallel to and spaced inward from sides 126, 128 of tray 104.

Locking plates 308A, 308B are configured to pivot into locking plate receiving apertures 316A, 316B to move retaining flanges 304A, 304B into the open position. Locking plate receiving aperture 316A is between proximal locking plate retaining post 310A and distal locking plate retaining post 312A. Similarly, locking plate receiving aperture 316B is between proximal locking plate retaining post 310B and distal locking plate retaining post 312B.

Proximal locking plate retaining post 310A and distal locking plate retaining post 312A are spaced apart from side 126 of tray 104 and project upward from base 302 in a direction opposite bottom surface 122 of tray 104. Similarly, proximal locking plate retaining post 310B and distal locking plate retaining post 312B are spaced apart from side 128 of tray 104 and project upward from base 302 in a direction opposite bottom surface 122 of tray 104. Locking plates 308A, 308B can pivot through locking plate receiving apertures 316A, 316B and outward past retaining posts 310A, 310B, 312A, 312B giving a greater range of motion of locking plates 308A, 308B and wider opening of retaining flanges 304A, 304B.

As illustrated in FIGS. 3 and 4, device removal assist card 112 is positioned between locking plates 308A, 308B and locking plate receiving apertures 316A, 316B to secure retaining flanges 304A, 304B, respectively, in the locked position. More particularly, device removal assist card 112 extends from proximal locking plate retaining posts 310A, 310B, across locking plate receiving apertures 316A, 316B, and to distal locking plate retaining posts 312A, 312B. This prevents unintentional motion of retaining flanges 304A, 304B thus avoiding unintentional and premature release of delivery system 114.

Specifically, device removal assist card 112 includes a first key 318A and a second key 318B, sometimes collectively referred to as a key. Keys 318A, 318B are flat sheet like members. First key 318A extends from proximal locking plate retaining post 310A, across locking plate receiving aperture 316A, and to distal locking plate retaining post 312A. First key 318A is located in a key slot 320A between retaining posts 310A, 312A and locking plate 308A. Stated another way, first key 318A is interposed and sandwiched between retaining posts 310A, 312A and locking plate 308A to hold locking plate 308A in place.

Similarly, second key 318B extends from proximal locking plate retaining post 310B, across locking plate receiving aperture 316B, and to distal locking plate retaining post 312B. Second key 318B is located in a key slot 320B between retaining posts 310B, 312B and locking plate 308B. Stated another way, second key 318B is interposed and sandwiched between retaining posts 310B, 312B and locking plate 308B to hold locking plate 308B in place.

Device removal assist card 112 can be similar to device removal assist card 812 as discussed below in reference to FIGS. 8-14 below. However, device removal assist card can be configured in any one of a number of ways to provide a removable key to lock and unlock device retention mechanism 134.

Figure 5:
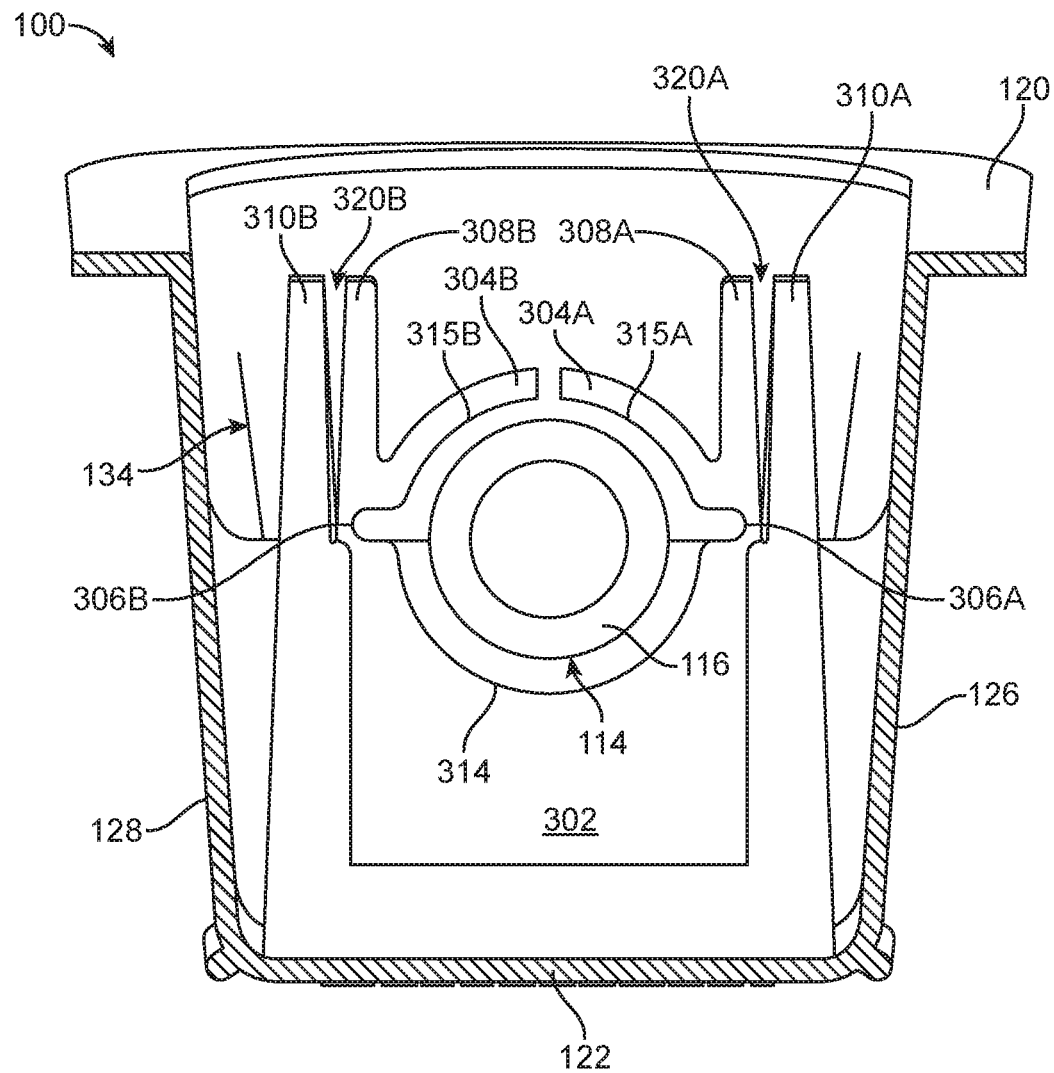
FIG. 5 is a cross-sectional front plan view of the device retention mechanism of FIGS. 3-4 after removal of a device removal assist card in accordance with one embodiment.
Figure 6:
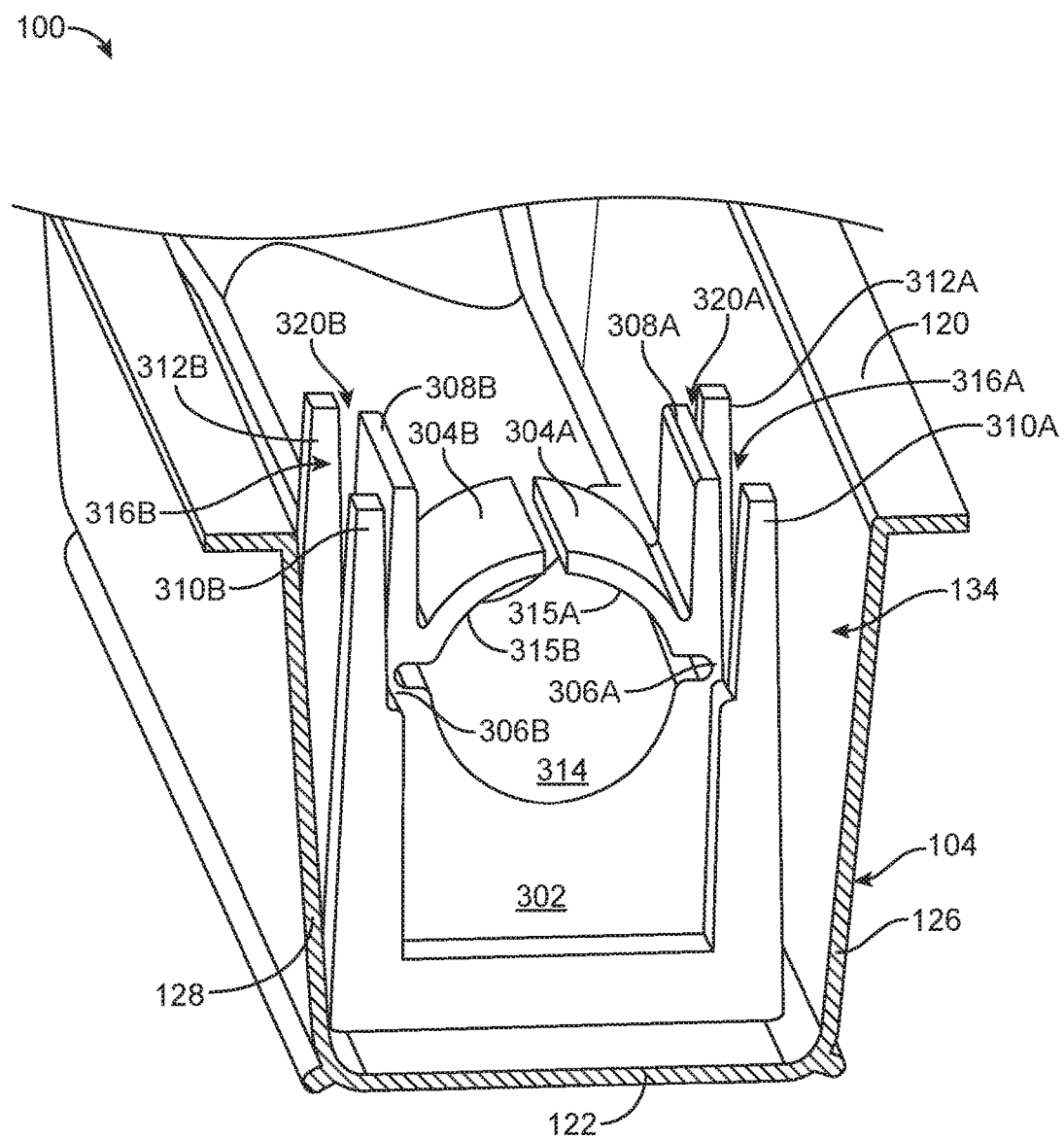
FIG. 6 is a perspective cross-sectional view of the device retention mechanism of FIG. 5 in accordance with one embodiment.

FIG. 5 is a cross-sectional front plan view of device retention mechanism 134 of FIGS. 3-4 after removal of device removal assist card 112 in accordance with one embodiment. FIG. 6 is a perspective cross-sectional view of device retention mechanism 134 of FIG. 5 in accordance with one embodiment. In FIGS. 5-6, device removal assist card 112 has been removed during the process of deploying handle 116. Further, in FIG. 6, handle 116 has been removed from the figure to allow visualization of device retention mechanism 134 although those of skill in the art will understand that handle 116 would exist in the view of FIG. 6 at the stage of deployment of handle 116 of FIG. 6.

FIGS. 5 and 6 illustrate device retention mechanism 134 after removal of device removal assist card 112. As illustrated, once device removal assist card 112 is removed, an open pathway of locking plates 308A, 308B into locking plate retaining apertures 316A, 316B is presented. More particularly, keys 318A, 318B of device removal assist card 112 are removed from key slots 320A, 320B This allows retaining flanges 304A, 304B to pivot around pivots 306A, 306B moving locking plates 308A, 308B into and through locking plate retaining apertures 308A, 308B thus releasing delivery system 114 for removal as illustrated in FIG. 7.

Figure 7:
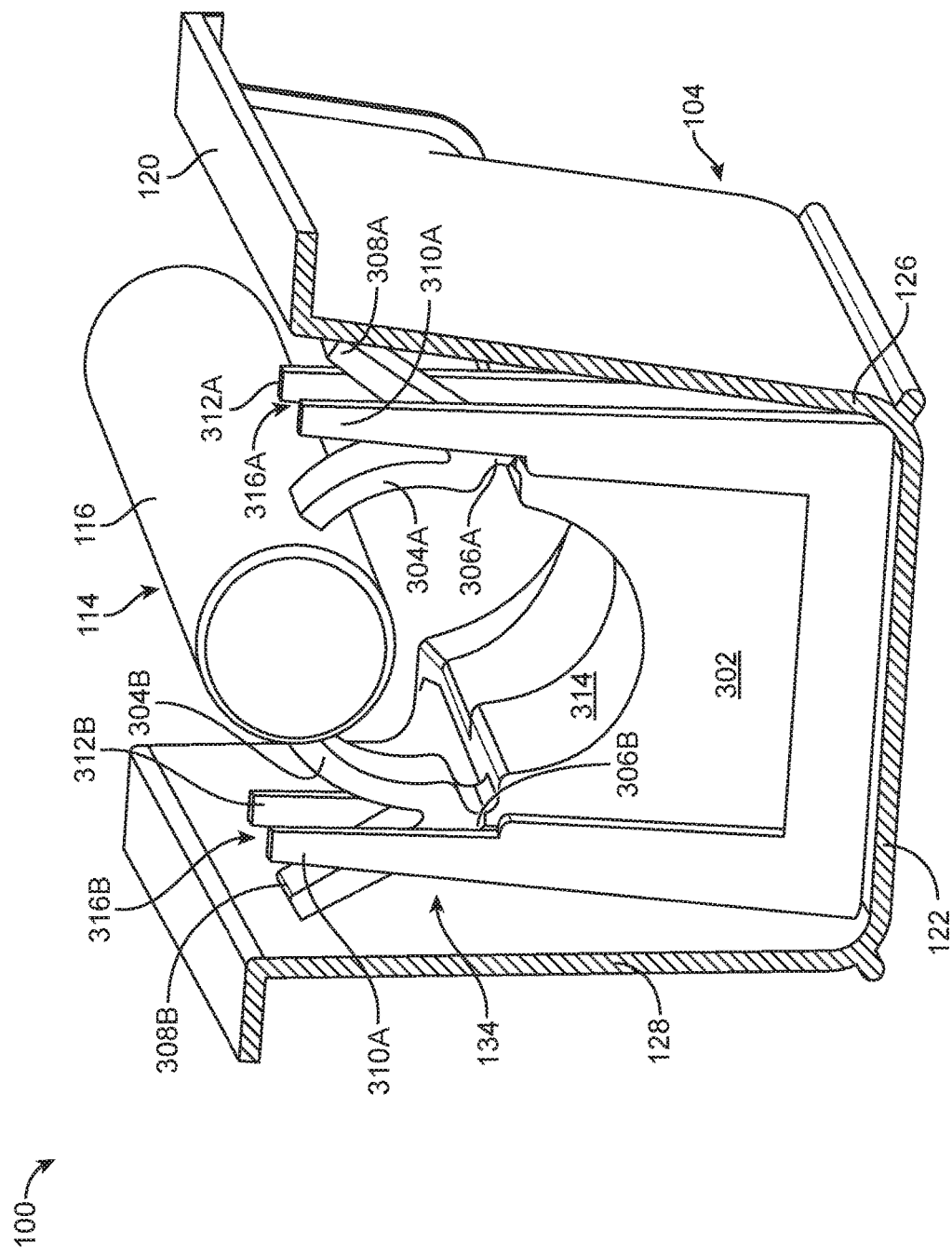
FIG. 7 is a perspective cross-sectional view of the handle being removed from the device retention mechanism of FIGS. 5-6 in accordance with one embodiment.

FIG. 7 is a perspective cross-sectional view of handle 116 being removed from device retention mechanism 134 of FIGS. 5-6 in accordance with one embodiment. Referring to FIG. 7, device retention mechanism 134 in the open position in accordance with this embodiment. As illustrated, locking plates 308A, 308B have been moved into locking plate receiving apertures 316A, 316B thus releasing delivery system 114 from retaining flanges 304A, 304B and generally from device retention mechanism 134.

Device retention mechanism 134 requires no user interaction. In other words, the lock of device retention mechanism 134 is removed without user interaction as part of the simple unloading procedure of moving the device removal assist card 112. Further, device retention mechanism 134 provides quality and consistency in retaining with minimal dependence on friction and part tolerance.

Device retention mechanism 134 eliminates accidental dislodgement and damage of delivery system 114, e.g., during transportation, as removal of a mechanical key (e.g., device removal assist card 112) is required. Further, device retention mechanism 134 has less potential for damaging delivery system 114 during removal as compared to a variable interference fit which sometimes requires excess force to remove. Device retention mechanism 134 is portable to other long catheter hybrid tray applications and not limited to the embodiments illustrated herein.

Figure 8:
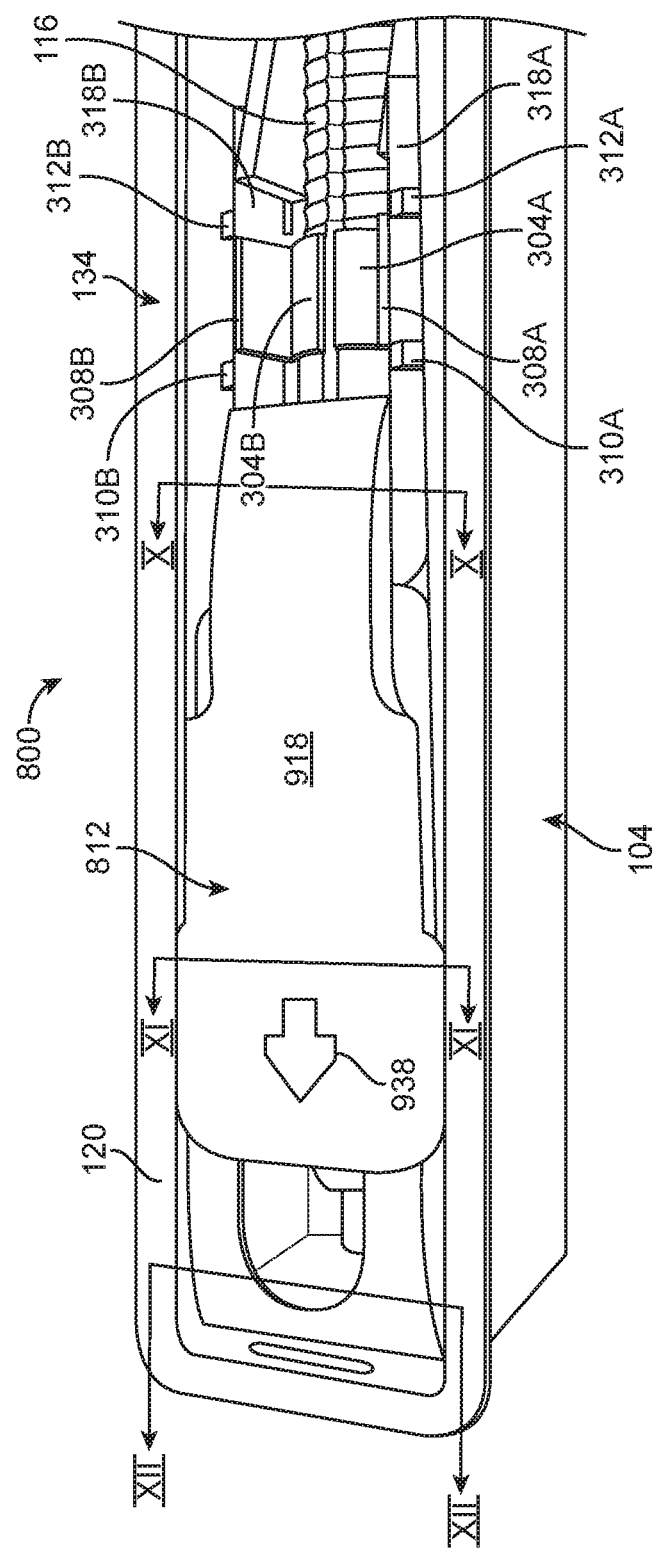
FIG. 8 is a top perspective view of a catheter delivery system package including a device removal assist card after removal of a lid in accordance with another embodiment.

FIG. 8 is a top perspective view of a catheter delivery system package 800 including a device removal assist card 812, sometimes called a slip card, after removal of a lid in accordance with another embodiment. Catheter delivery system package 800 of FIG. 8 is similar to catheter delivery system package 100 of FIGS. 1-7 and only the significant differences are discussed below. Referring to FIG. 8, lid 110 (see FIG. 2) has been removed to expose device removal assist card 812.

Figure 9:
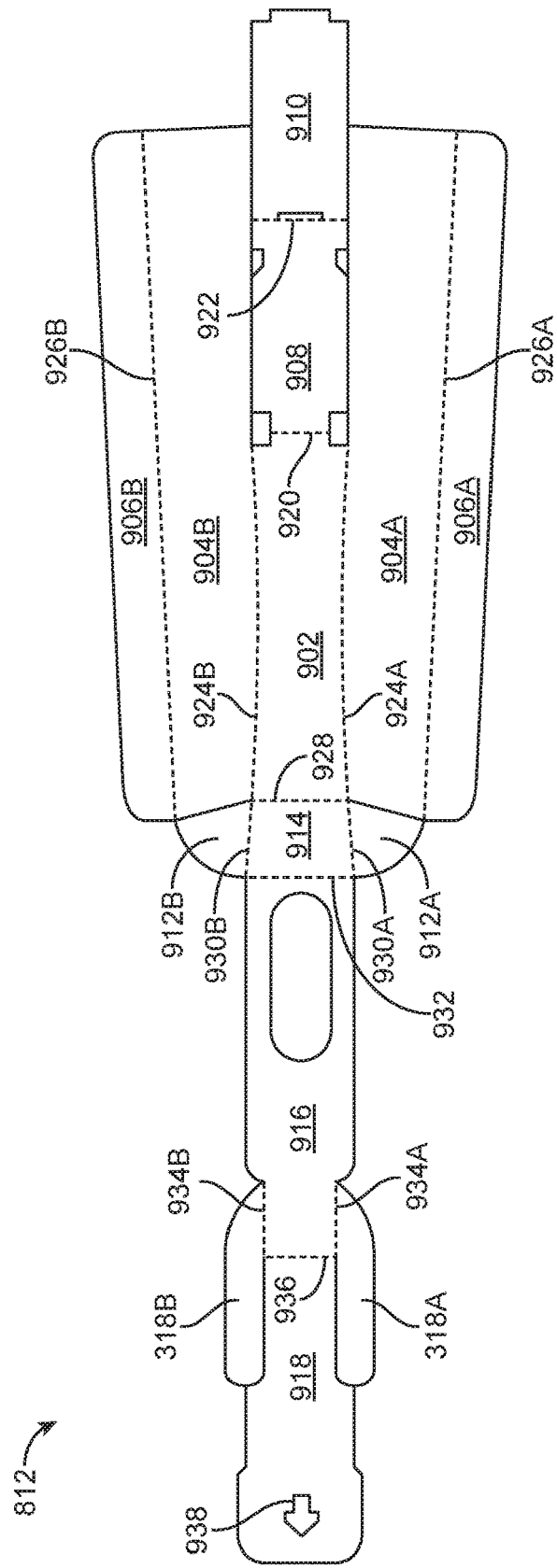
FIG. 9 is a laid out plan view of the device removal assist card of the catheter delivery system package of FIG. 8 in accordance with one embodiment.

FIG. 9 is a laid out plan view of device removal assist card 812 of catheter delivery system package 800 of FIG. 8 in accordance with one embodiment. As is illustrated in FIG. 9, device removal assist card 812 includes a base 902, inner sidewalls 904A, 904B, outer sidewalls 906A, 906B, inner base flap 908, outer base flap 910, corner flaps 912A, 912B, pull tab connection flap 914, pull tab body flap 916, keys 318A, 318B, and pull tab 918. In FIG. 9, a solid line indicates a cut line and a dashed line includes a fold line. Base 902, inner sidewalls 904A, 904B, outer sidewalls 906A, 906B, inner base flap 908, outer base flap 910, corner flaps 912A, 912B, pull tab connection flap 914, pull tab body flap 916, keys 318A, 318B, and pull tab 918 are planar rigid surfaces in accordance with one embodiment.

A fold in the lengthwise direction parallel to the longitudinal axis of delivery system 114 and the length of tray 104 is hereinafter referred to as a lengthwise fold. A fold in the sideways direction perpendicular to the lengthwise direction and parallel to the radial direction of delivery system 114 and the width of tray 104 is hereinafter referred to as a sideway fold. In light of this disclosure, it is to be understood that the folds may not be exactly straight and may not be exactly parallel or perpendicular to the length of tray 104. Further, although various features may be referred to as parallel or perpendicular, it is understood that the features may not be exactly parallel or perpendicular but are substantially parallel or perpendicular.

Inner base flap 908 is connected to base 902 by a sideways inner base flap fold 920. Outer base flap 910 is connected to inner base flap 908 at a sideways outer base flap fold 922. Inner sidewalls 904A, 904B are connected to base 902 by lengthwise inner sidewall folds 924A, 924A. Outer sidewalls 906A, 906B are connected to inner sidewalls 904A, 904B by lengthwise outer sidewall folds 926A, 926B.

Pull tab connection flap 914 is connected to base 902 by a sideways pull tab connection flap fold 928. Corner flaps 912A, 912B are connected to pull tab connection flap 914 by lengthwise corner flap folds 930A, 930B. Pull tab body flap 916 is connected to pull tab connection flap 914 by a sideways pull tab body flap fold 932.

Keys 318A, 318A are connected to pull tab body flap 916 by lengthwise key folds 934A, 934B. Pull tab 918 is connected to pull tab body flap 916 by a sideways pull tab fold 936.

Figure 11:
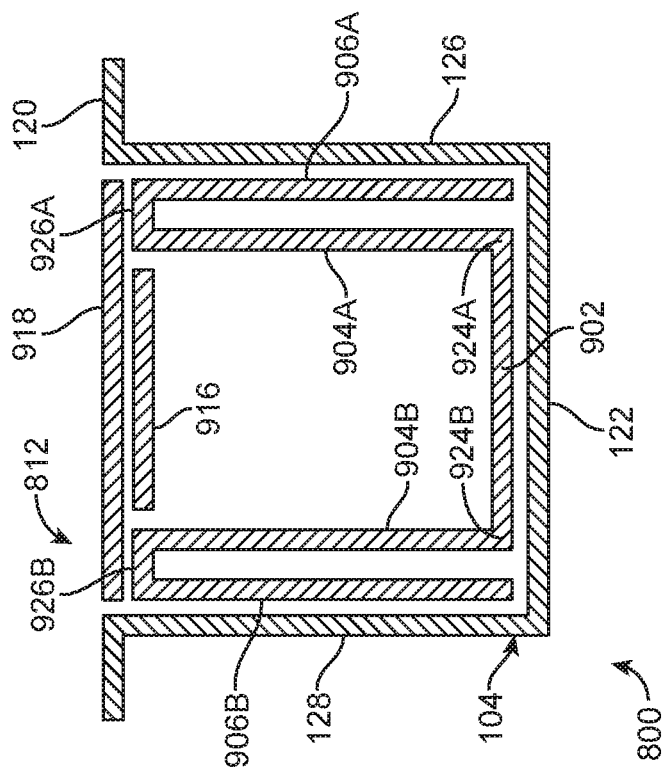
FIG. 11 is a cross-sectional view of the catheter delivery system package of FIG. 8 along the line XI-XI in accordance with one embodiment.
Figure 10:
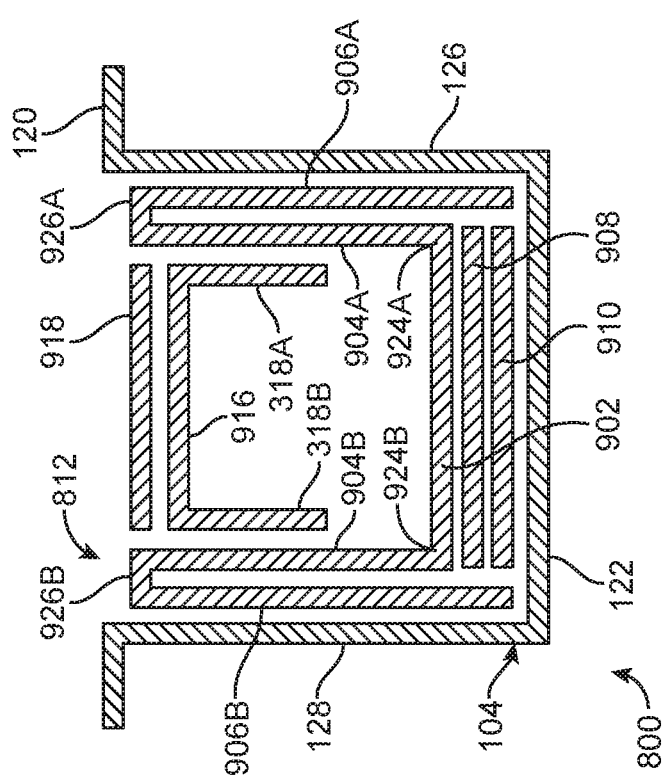
FIG. 10 is a cross-sectional view of the catheter delivery system package of FIG. 8 along the line X-X in accordance with one embodiment.
Figure 12:
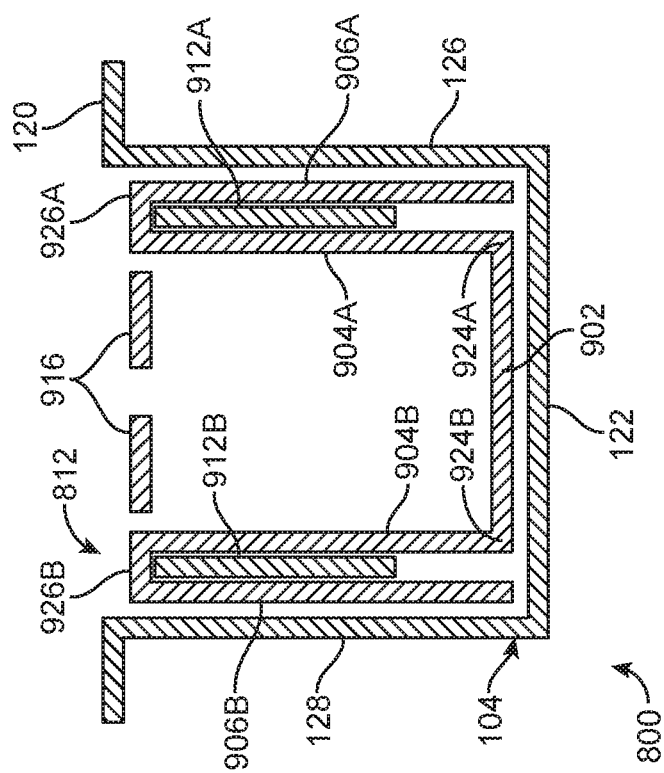
FIG. 12 is a cross-sectional view of the catheter delivery system package of FIG. 8 along the line XII-XII in accordance with one embodiment.

FIG. 10 is a cross-sectional view of catheter delivery system package 800 of FIG. 8 along the line X-X in accordance with one embodiment. FIG. 11 is a cross-sectional view of catheter delivery system package 800 of FIG. 8 along the line XI-XI in accordance with one embodiment. FIG. 12 is a cross-sectional view of catheter delivery system package 800 of FIG. 8 along the line XII-XII in accordance with one embodiment. In FIGS. 10, 11, and 12, only device removal assist card 812 and tray 104 are illustrated for clarity.

When loaded in tray 104, base 902 is parallel to and adjacent to bottom surface 122 of tray 104. Outer base flap 910 is folded at fold 922 upward and over until it lies parallel on top of inner base flap 908. Outer base flap 910 and inner base flap 908 are then folded in tandem at fold 920 downward and over until both flaps lie parallel to base 902. Inner base flap 908 and outer base flap 910 are both visible in their folded positions in FIG. 10.

Inner sidewalls 904A, 904B are folded at inner sidewall folds 924A, 924B from base 902 to extend perpendicularly upward from base 902. Outer sidewalls 906A, 906B are folded at outer sidewall folds 926A, 926B from inner sidewalls 904A, 904B to extend downward parallel to inner sidewalls 904A, 904B. Outer sidewalls 906A, 906B are adjacent to and parallel to sides 126, 128 of tray 104.

Pull tab connection flap 914 is folded at pull tab connection flap fold 928 from base 902 to extend perpendicularly upward from base 902. Pull tab connection flap 914 is directly adjacent and parallel to proximal end 124 of tray 104. Corner flaps 912A, 912B are folded at corner flap folds 930A, 930B from pull tab connection flap 914. Corner flaps 912A, 912B extend perpendicularly from pull tab connection flap 914 to be parallel to, and between, inner sidewalls 904A, 904B, and outer side walls 906A, 906B.

Pull tab body flap 916 is folded at pull tab body flap fold 932 from pull tab connector flap 914. Pull tab body flap 916 is parallel to bottom surface 122 of tray 104 and is recessed slightly below lid sealing flange 120.

Keys 318A, 318B are folded at key folds 934A, 934B from pull tab body flap 916. Keys 318A, 318B are located inwards of inner sidewalls 904A, 904B and are parallel to sides 126, 128 of tray 104. Keys 318A, 318B project distally to lock device retention mechanism 134 as illustrated and discussed above in reference to FIGS. 3 and 4.

Pull tab 918 if folded at pull tab fold 936 from pull tab body flap 916. Pull tab 918 include an arrow shaped opening 938 therein to indicate the direction that pull tab 918 should be pulled to removed delivery system 114.

Figure 13:
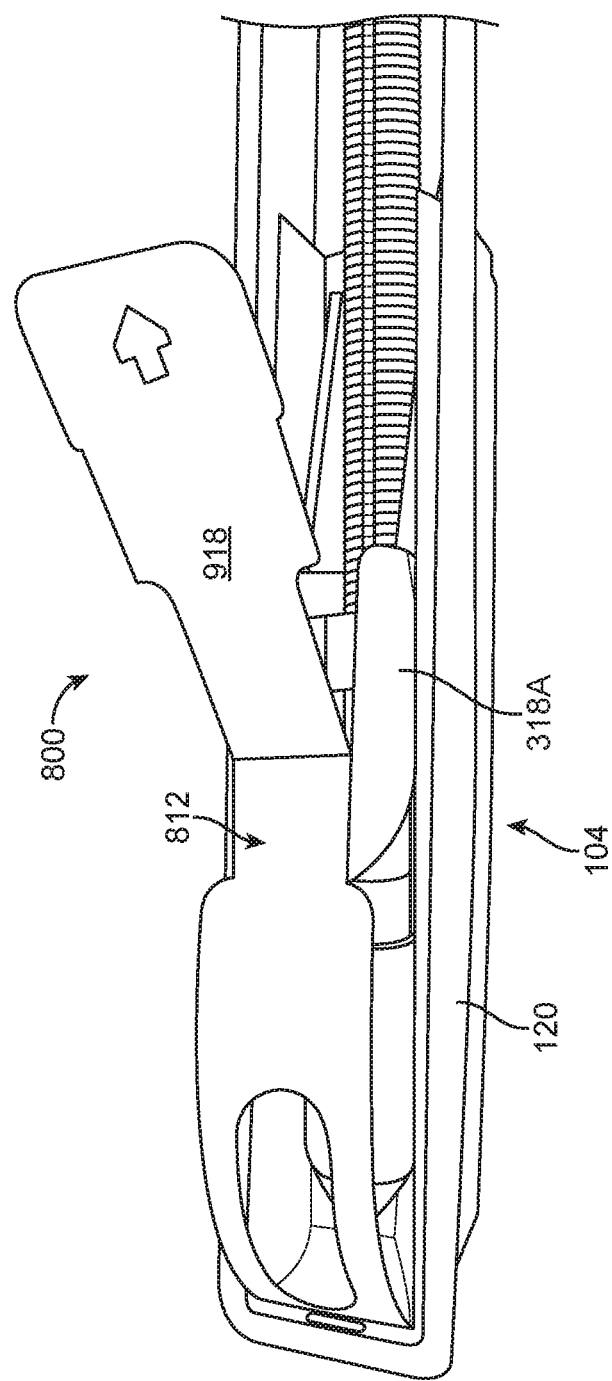
FIG. 13 is a perspective view of the catheter delivery system package of FIG. 8 illustrating a stage where keys are just disengaging a device retention mechanism in accordance with one embodiment.

FIG. 13 is a perspective view of catheter delivery system package 800 of FIG. 8 illustrating a stage where keys 318A, 318B are just disengaging device retention mechanism 134 in accordance with one embodiment. Referring to FIG. 13, after partial or complete removal of lid 110 by the circulating nurse or other user, pull tab 918 is pulled by the scrub nurse or other staff member in the sterile field. This removes keys 318A, 318B from device retention mechanism 134 as illustrated and discussed above in reference to FIGS. 5 and 6. Removal of keys 318A, 318B from device retention mechanism 134 allows retaining flanges 304A, 304B to freely pivot around pivots 306A, 306B to release handle 116 of delivery system 114.

Figure 14:
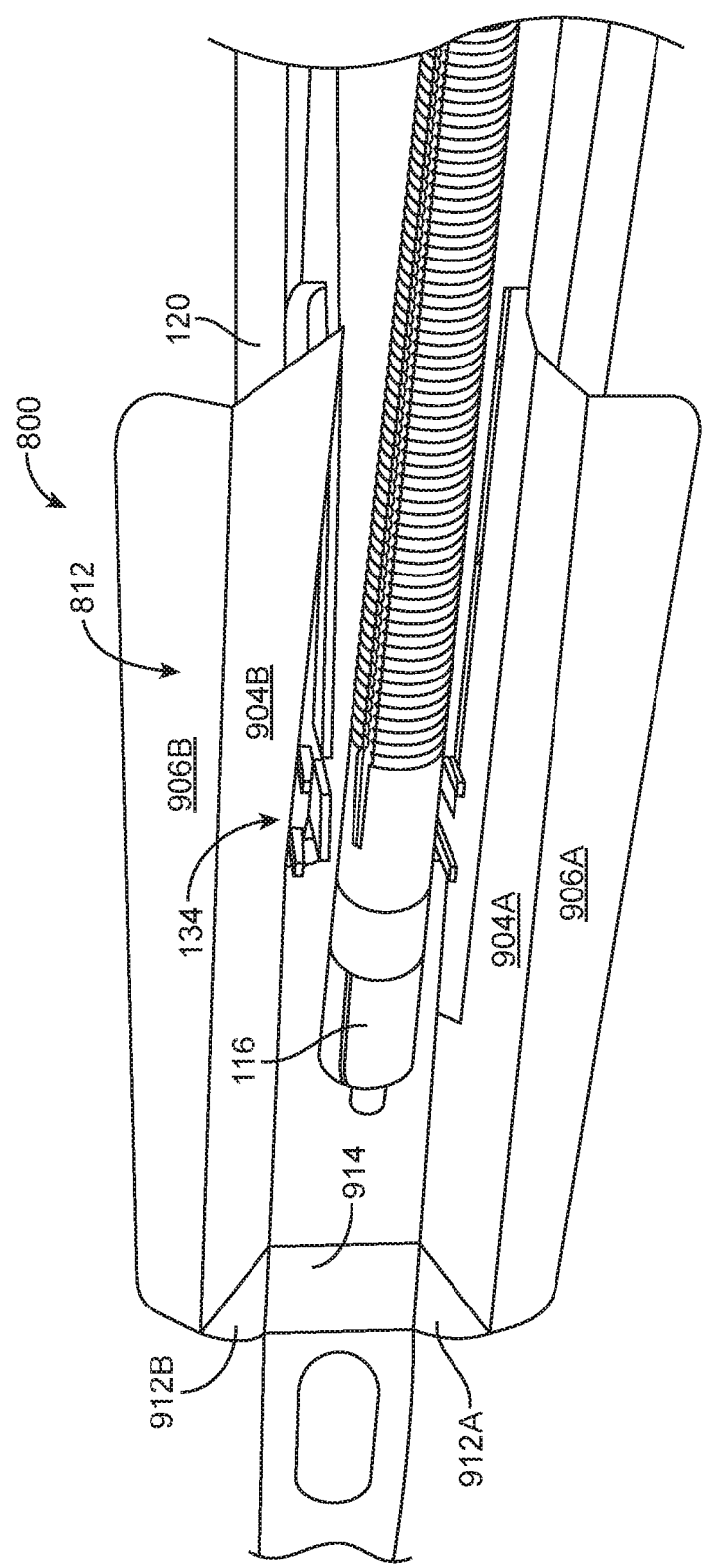
FIG. 14 is a perspective view of the catheter delivery system package of FIG. 13 at a later stage during removal of the delivery system in accordance with one embodiment.

FIG. 14 is a perspective view of catheter delivery system package 800 of FIG. 13 at a later stage during removal of delivery system 114 in accordance with one embodiment. Referring to FIG. 14, pull tab 918 is further pulled by the scrub nurse or other staff member in the sterile field. This raises device removal assist card 812 from tray 104.

As outer sidewalls 906A, 906B are raised above lid sealing flange 120, outer sidewalls 906A, 906B project outward and above lid sealing flange 120. At the same time, pull tab connection flap 914 is pulled above lid sealing flange 120. Corner flaps 912A, 912B project from pull tab connection flap 914 to inner sidewalls 904A, 904B. Accordingly, device removal assist card 812 extends over lid sealing flange 120 preventing contact between delivery system 114 and lid sealing flange 120. Lid sealing flange 120 is considered a non-sterile surface in accordance one embodiment and thus contact between delivery system 114 or personnel within the sterile field and lid sealing flange 120 must be prevented.

At the same time, as device removal assist card 812 is raised from tray 104, device removal assist card 812, e.g., base 902 thereof, contacts and raises handle 116. As keys 318A, 318B have been removed from device retention mechanism 134, retaining flanges 304A, 304B moved to the open position as illustrated in FIG. 7 thus releasing handle 116.

Handle 116 is then grasped by the scrub nurse or other staff member in the sterile field and delivery system 114 is removed from catheter delivery system package 800.

Figure 15:
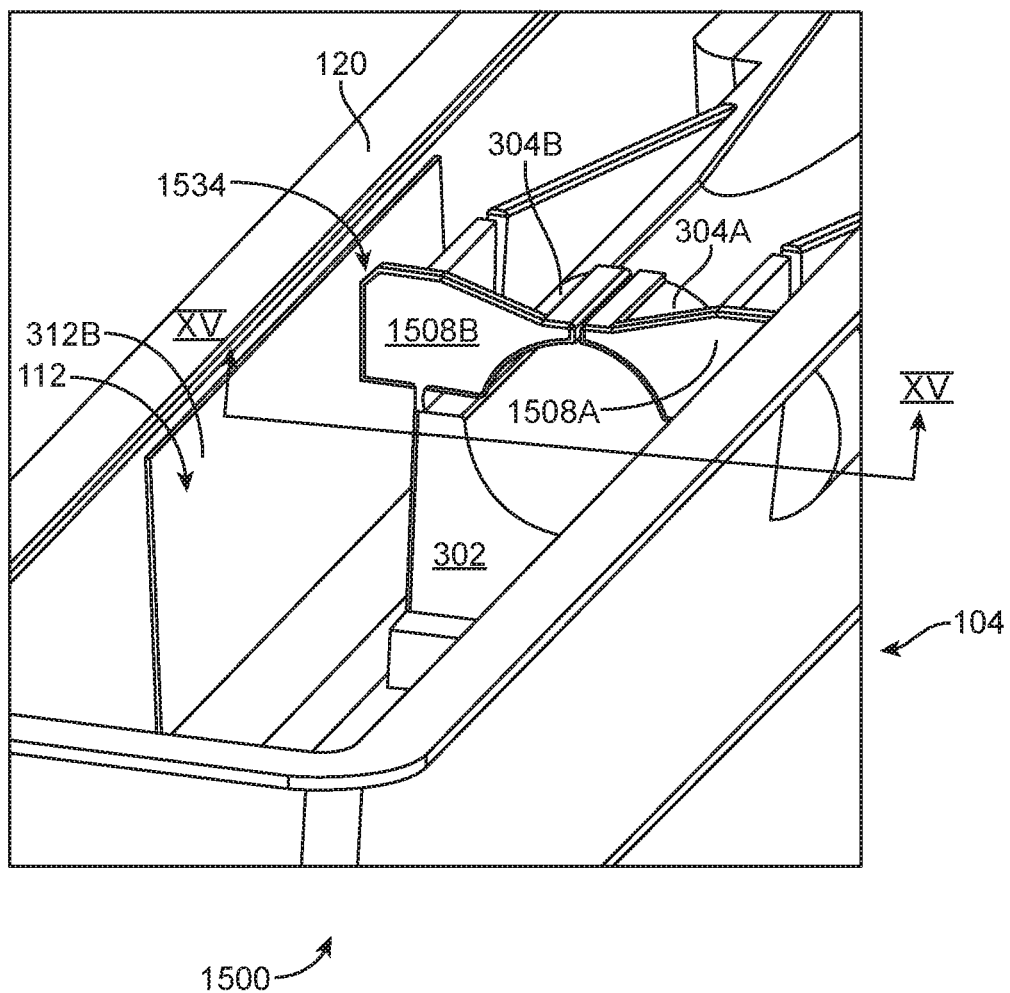
FIG. 15 is a perspective view of a catheter delivery system package having a device retention mechanism in accordance with another embodiment.
Figure 16:
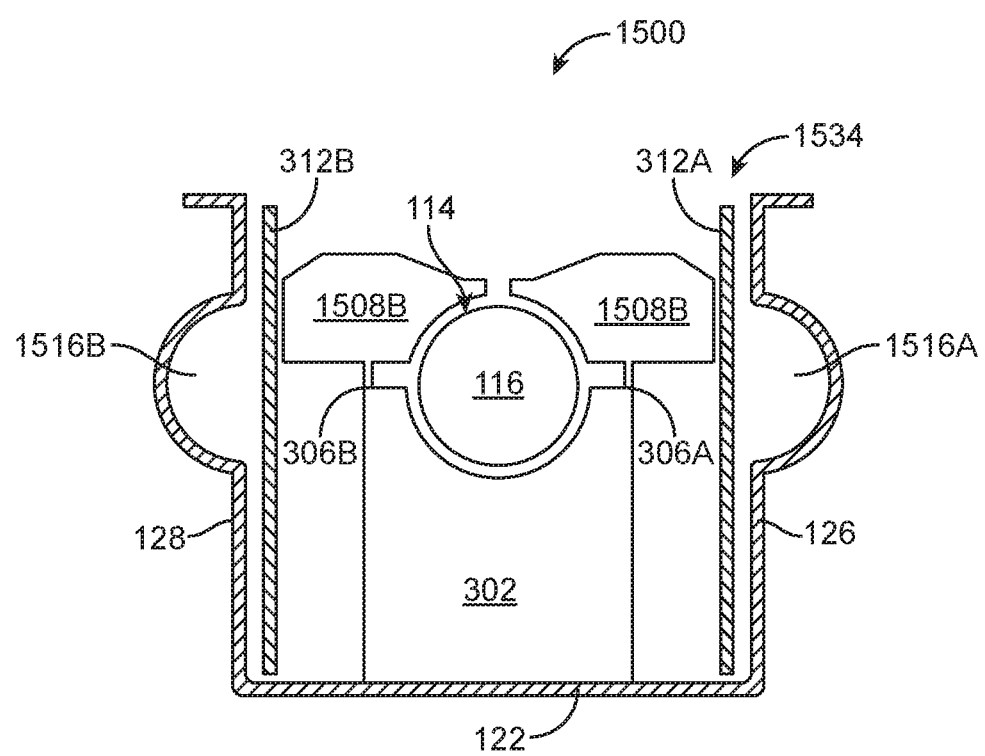
FIG. 16 is a cross-sectional view of the catheter delivery system package of FIG. 15 along the line XV-XV in accordance with one embodiment.

FIG. 15 is a perspective view of a catheter delivery system package 1500 having a device retention mechanism 1534 in accordance with another embodiment. FIG. 16 is a cross-sectional view of catheter delivery system package 1500 of FIG. 15 along the line XV-XV in accordance with one embodiment. In FIG. 15, handle 116 of delivery system 114 has been removed to allow visualization of device retention mechanism 1534. Catheter delivery system package 1500 including device retention mechanism 1534 of FIGS. 15 and 16 is similar to catheter delivery system package 100 including device retention mechanism 134 of FIGS. 1 through 7 and only the significant differences are discussed.

Referring now to FIGS. 15 and 16 together, device retention mechanism 1534 includes fixed base 302, retaining flanges 304A, 304B, pivots 306A, 306B, locking plates 1508A, 1508B, and locking plate receiving apertures 1516A, 1516B.

Locking plates 1508A, 1508B are integral parts of retaining flanges 304A, 304B in accordance with this embodiment. Locking plates 1508A, 1508B extend sideways in a common plane in accordance with this embodiment and are configured to pivot into locking plate receiving apertures 1516A, 1516B to move retaining flanges 304A, 304B into the open position. In one embodiment, locking plates 1508A, 1508B need not be in a common plane as required by the profile or protruding feature defining the delivery system 114.

Locking plate receiving apertures 1516A, 1516B are formed in sides 126, 128 of tray 104, e.g., by molding. Device removal assist card 112 (or 832 or other key) is positioned between locking plates 1508A, 1508B and locking plate receiving apertures 1516A, 1516B to secure retaining flanges 304A, 304B in the locked position. This prevents unintentional motion of retaining flanges 304A, 304B thus avoiding unintentional and premature release of delivery system 114.

Figure 17:
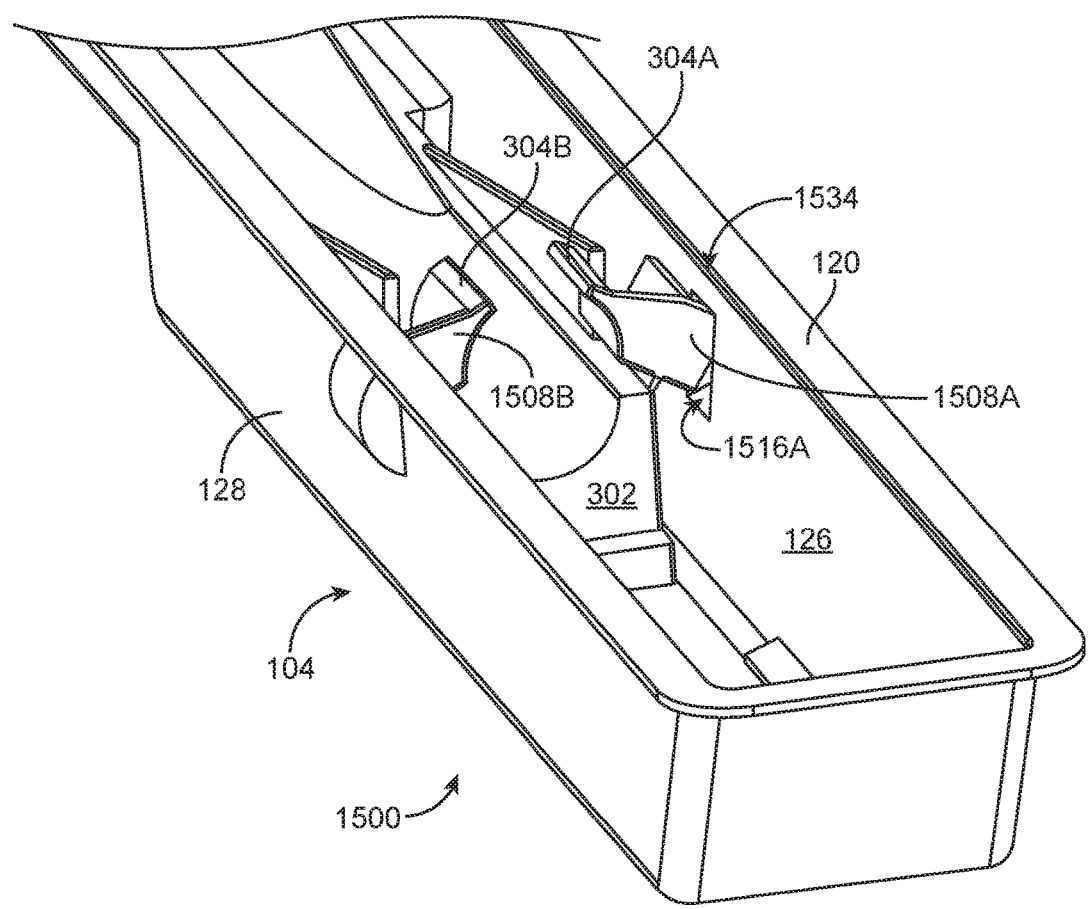
FIG. 17 is a perspective view of the catheter delivery system package of FIGS. 15-16 after removal of a device removal assist card in accordance with another embodiment.

FIG. 17 is a perspective view of catheter delivery system package 1500 of FIGS. 15-16 after removal of device removal assist card 112 and delivery system 114 in accordance with another embodiment.

As illustrated, once device removal assist card 112 is removed, an open pathway of locking plates 1508A, 1508B into locking plate receiving apertures 1516A, 1516B is presented. This allows retaining flanges 304A, 304B to pivot moving locking plates 1508A, 1508B into locking plate receiving apertures 1516A, 1516B thus releasing delivery system 114 for removal as illustrated in FIG. 17.

Figure 18:
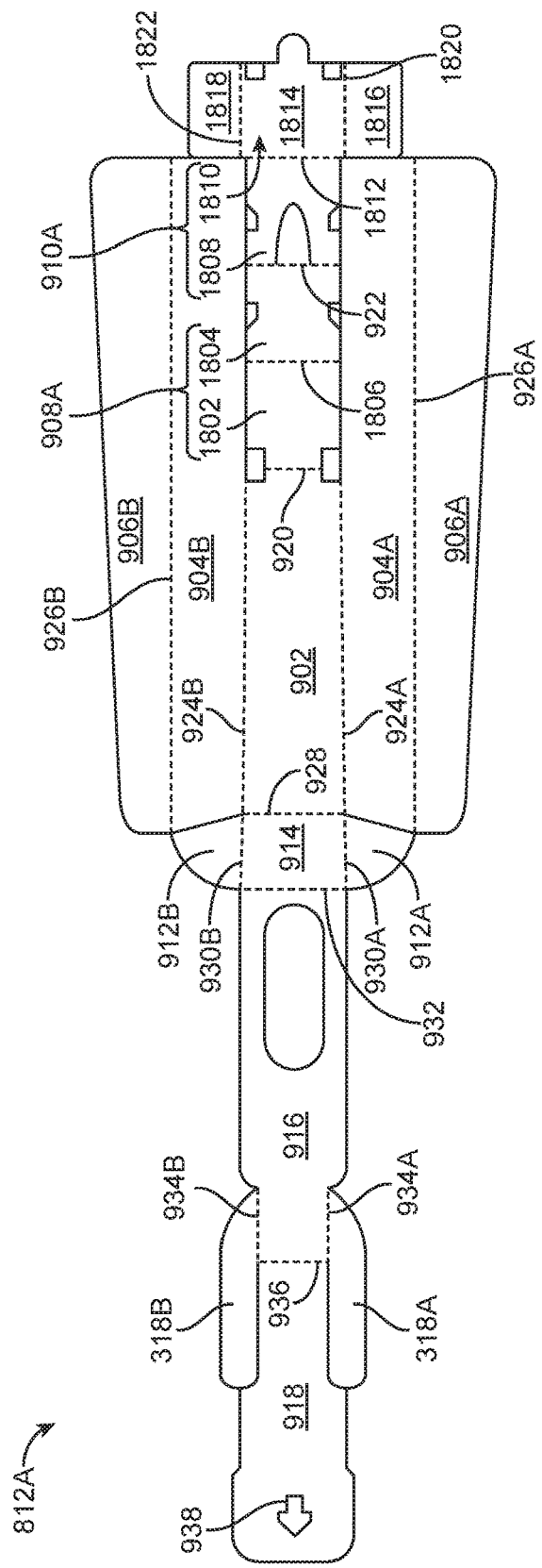
FIG. 18 is a laid out plan view of a device removal assist card of a catheter delivery system package in accordance with yet another embodiment.

FIG. 18 is a laid out plan view of a device removal assist card 812A of a catheter delivery system package in accordance with yet another embodiment. Device removal assist card 812A of FIG. 18 is similar to device removal assist card 812 of FIG. 9 and loaded and used in a similar manner as that described above. Only the significant differences between device removal assist card 812A of FIG. 18 and device removal assist card 812 of FIG. 9 are discussed below.

In accordance with this embodiment, an inner base flap 908A includes inner base flap segments 1802, 1804. Inner base flap segment 1802 is connected to base 902 by inner base flap fold 920. Inner base flap segment 1804 is connected to inner base flap segment 1802 by an inner base flap segment fold 1806.

An outer base flap 910A includes outer base flap segments 1808, 1810. Outer base flap segment 1808 is connected to inner base flap segment 1804 by outer base flap fold 922. Outer base flap segment 1810 is connected to outer base flap segment 1808 by an outer base flap segment fold 1812.

Outer base flap segment 1810 includes an outer base flap segment base 1814 and outer base flap segment sidewalls 1816, 1818 folded from outer base flap segment base 1814 at lengthwise outer base flap segment sidewall folds 1820, 1822. In one embodiment, outer base flap segment sidewalls 1816, 1818 facilitate outward projection of outer sidewalls 906A, 906B during removal of delivery system 114.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A device retention mechanism comprising:
   a base;
   a tray, the base being coupled to the tray;
   retaining flanges;
   pivots coupling the retaining flanges to the base;
   locking plates coupled to the retaining flanges such that the retaining flanges and the locking plates are pivotally coupled to the base by the pivots; and
   locking plate apertures configured to receive the locking plates, wherein the tray comprises the locking plate apertures, wherein the locking plates are spaced apart from the locking plate apertures when the retaining flanges are in a closed position,
   wherein the base comprises a device retaining surface configured to receive a delivery system,
   wherein the retaining flanges comprise device retaining surfaces configured to receive the delivery system,
   wherein the device retaining surface of the base and the device retaining surfaces of the retaining flanges collectively define a cylindrical surface.

2. The device retention mechanism of claim 1 wherein the retaining flanges are adjacent one another with a gap in between when in the closed position.

3. The device retention mechanism of claim 1 wherein the locking plates lie in a common plane.

4. A device retention mechanism comprising:
   a base;
   retaining flanges;
   pivots coupling the retaining flanges to the base;
   locking plates coupled to the retaining flanges;
   locking plate apertures configured to receive the locking plates; and
   a device removal assist card configured to prevent the locking plates from entering into the locking plate apertures.

5. The device retention mechanism of claim 4 wherein the device removal assist card is located between the locking plates and the locking plate apertures.

6. The device retention mechanism of claim 5 wherein the device removal assist card is removable to allow the locking plates to access the locking plate apertures.

7. The device retention mechanism of claim 4 further comprising:
   proximal locking plate retaining posts;
   distal locking plate retaining posts, wherein the locking plate apertures are between the proximal locking plate retaining posts and the distal locking plate retaining posts.

* * * * *